US011062266B2

(12) United States Patent
Kishon et al.

(10) Patent No.: US 11,062,266 B2
(45) Date of Patent: Jul. 13, 2021

(54) METHOD AND SYSTEM FOR AN ONLINE PATIENT COMMUNITY BASED ON "STRUCTURED DIALOG"

(75) Inventors: Amir Kishon, New York, NY (US); Elad Levran, New York, NY (US)

(73) Assignee: Wellness Layers Inc., New York, NY (US)

(*) Notice: Subject to any disclaimer, the term of this patent is extended or adjusted under 35 U.S.C. 154(b) by 1211 days.

(21) Appl. No.: 12/981,621

(22) Filed: Dec. 30, 2010

(65) Prior Publication Data

US 2012/0173256 A1 Jul. 5, 2012

(51) Int. Cl.
| | |
|---|---|
| *G16H 80/00* | (2018.01) |
| *G06Q 10/10* | (2012.01) |
| *G06Q 50/22* | (2018.01) |
| *G06Q 30/00* | (2012.01) |
| *G06Q 50/00* | (2012.01) |

(52) U.S. Cl.
CPC .......... *G06Q 10/101* (2013.01); *G06Q 30/01* (2013.01); *G06Q 50/01* (2013.01); *G06Q 50/22* (2013.01); *G16H 80/00* (2018.01)

(58) Field of Classification Search
CPC ....... G06Q 50/01; G06F 16/22; G06F 16/335; G06N 5/04; G06N 20/00; G06N 5/046
USPC .......................................................... 705/2
See application file for complete search history.

(56) References Cited

U.S. PATENT DOCUMENTS

| | | | | |
|---|---|---|---|---|
| 2003/0093419 A1* | 5/2003 | Bangalore | .......... | G01C 21/3679 |
| 2004/0128165 A1* | 7/2004 | Block | ..................... | G16H 10/60 |
| | | | | 705/2 |
| 2008/0306770 A1* | 12/2008 | Sysko | ..................... | G16H 20/60 |
| | | | | 705/3 |
| 2010/0070554 A1* | 3/2010 | Richardson | ............ | G06Q 10/06 |
| | | | | 709/202 |
| 2010/0076786 A1* | 3/2010 | Dalton | ..................... | G16H 10/60 |
| | | | | 705/3 |
| 2011/0161095 A1* | 6/2011 | Line | ........................ | G16H 10/60 |
| | | | | 705/2 |
| 2011/0161110 A1* | 6/2011 | Mault | ..................... | G16H 40/67 |
| | | | | 705/3 |

* cited by examiner

*Primary Examiner* — Reginald R Reyes
(74) *Attorney, Agent, or Firm* — The Roy Gross Law Firm, LLC; Roy Gross

(57) ABSTRACT

A system for an online community based on Structured Dialogs offering organizations the opportunity to create online communities and have a dialog with users on their status, condition, and progress without the risk of adverse event reports by users. The system may include an interface that limits user communication to Structured Dialogs comprising controlled vocabulary elements of specific choices, including pop-ups, drop downs, and sliders. The system includes a personal health and wellness management tool coupled with the community to enable the user to manage his or her medication and condition using Structured Dialogs and thus making the interaction more interesting and effective for users. The system may also include an information repository "Info" Layer that can offer articles that are relevant to users. The "We", "Me" and "Info" Layers can share statistics and Structured Dialogs data.

14 Claims, 12 Drawing Sheets

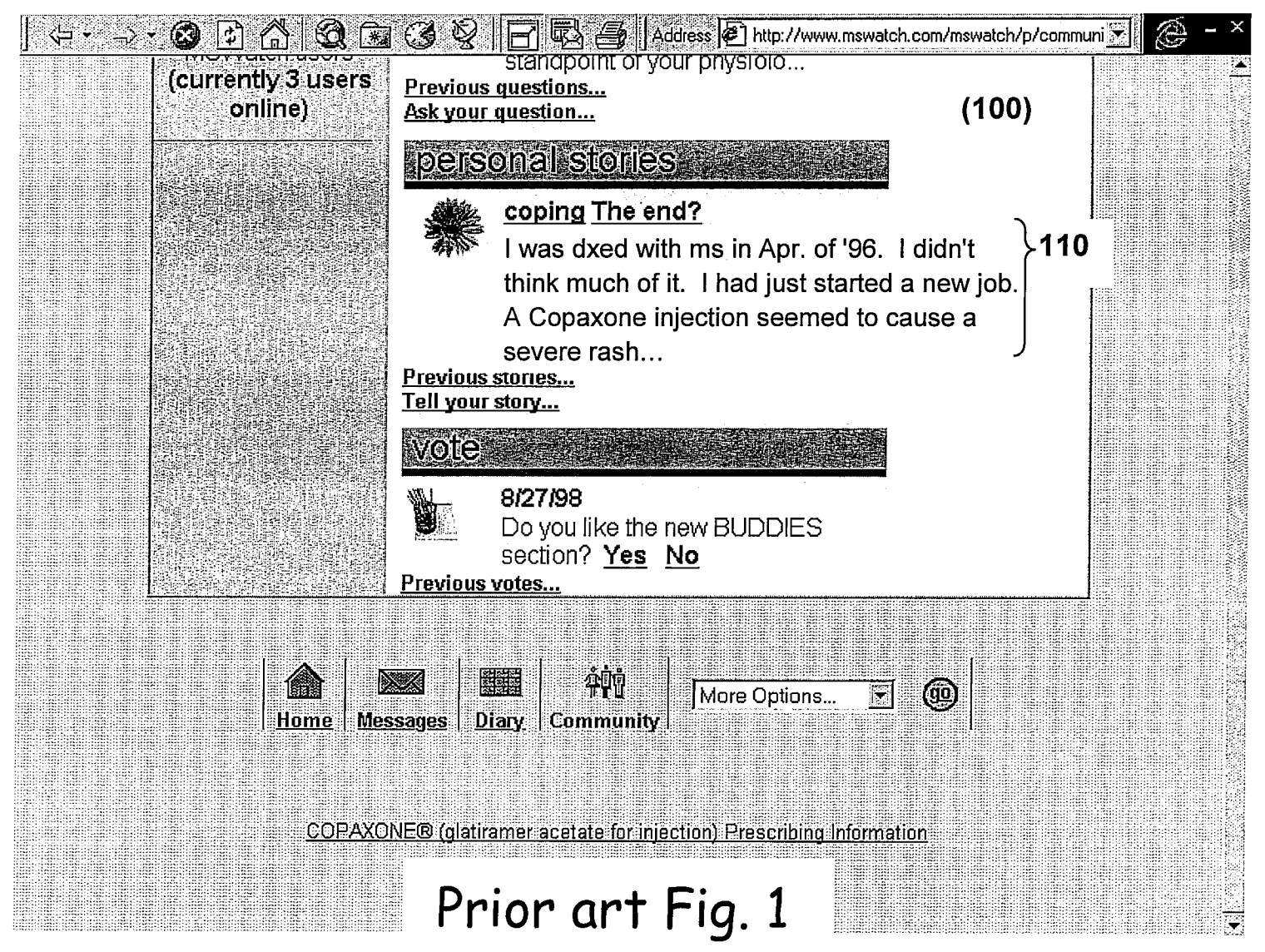

Prior art Fig. 1

How Can Yoga Help You Deal with Arthritis

Yoga Poses can help strengthen your joints which is crucial in preventing and dealing with arthritis. It makes your joints function normally, thus reducing the risk of stiffness. With its virtue of balance, Yoga practice helps regulate the levels of uric acid in the body. Obesity may also be avoided through the practice. More importantly, Yoga can lead to an overall healthier lifestyle that can enhance your resistance not only from arthritis but to other sicknesses as well.

Here are the basic Asanas which can help you in dealing with Arthritis:

Easy Pose
This is one of the classic Meditative Poses. The Easy Pose helps in straightening the spine, slowing down metabolism, promoting inner tranquility, and keeping your mind still.

Single Leg Raises
This Yoga Pose is performed prepares the body for other exercises. It benefits the legs, lower back muscles, and abdominal area. In practicing the Single Leg Raise, only one leg is raised.

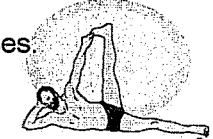

Shoulder Stretches
Shoulder Stretches are great in relieving stress and tension on your shoulders, as well as your entire upper back. Practice them daily for several weeks and notice the changes.

Neck Exercise
Many people hold tension in their necks and shoulders, leading to stiffness, bad posture, and tension headaches. Yoga practice can ease tension, increase flexibility, and tone the muscles..

Standing Side Stretch pose
The Standing Side Stretch is another Yoga Pose with two lines of energy radiating outward from your center. This is a wonderful stretch where one line of energy reaches upward from your belly and outward through the arm, and one line travels downward through the legs.

Hand Clenching
Hands and wrists are common body parts which are affected by Arthritis, especially Osteoarthritis. Keep your hands and joints and in 'good working condition' by performing the Hand Clenching Exercise.

Wrist Bending
Wrists can also be affected by arthritis, specifically Osteoarthritis and Rheumatoid Arthritis. Take good care of your wrists through stretching and bending. Learn how to improve the range of motion of your wrists by doing the Wrist Bending Exercise.

Why don't you give these Yoga Poses a try? They might be really helpful in dealing with Arthritis. Just take note that not all poses are advisable to be practiced by people with Arthritis. It may depend on their health condition and their ability to do certain poses. It would be better to consult a physician first or do the poses under the supervision of a Yoga instructor.

Community Wisdom
6 members who share your condition found this article helpful
15% of the members of the community reported that Yoga helped them.
You have done 15 times Yoga in the last 2 months burning total of 2500 calories } 510

Fig. 5

BUILD YOUR ARTHRITIS PLAN

One of the most important things you can do in order to improve your Arthritis Condition is to review your overall wellness activities and create your Healthy Living with Arthritis Plan. Let us help you to set up your plan by answering the following questions (don't worry, you can change any settings later on).

STEP 1: ABOUT YOU

610 — Have you been diagnosed by a doctor?
- ○ Not yet
- ● Yes
  - ○ I have Osteoarthritis
  - ● I have Rheumatoid Arthritis
  - ○ I have Ankylosing Spondylitis
  - ○ Other 620 — How long ago were you diagnosed?

| Newly Diagnosed | 1 yr ago | 2 yrs ago | 3 yrs ago | 4 yrs ago | 5 yrs ago | 6 yrs ago | 7 yrs ago | 8 yrs ago | 9 yrs ago | 10 yrs ago or more |

630 — What medications are you taking?
Type medication name: Brand A / Brand B ← 631 / Brand C / Brand D I take: 1. Brand W ← 632
       2. Brand X        ← 633

Have you made any changes to these categories to help improve your condition?

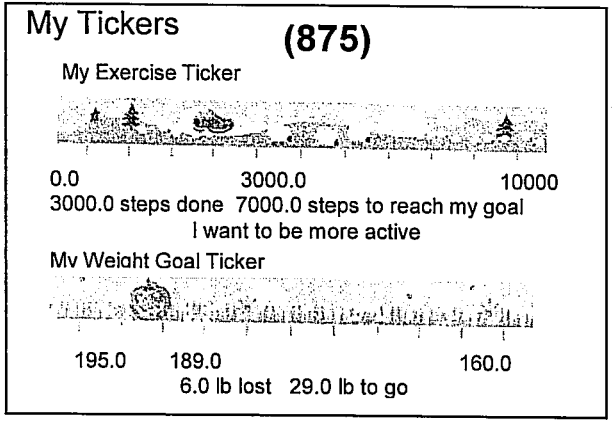
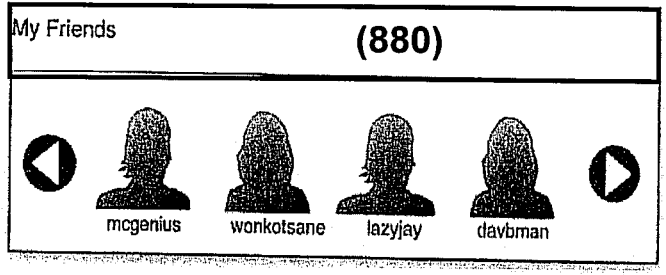
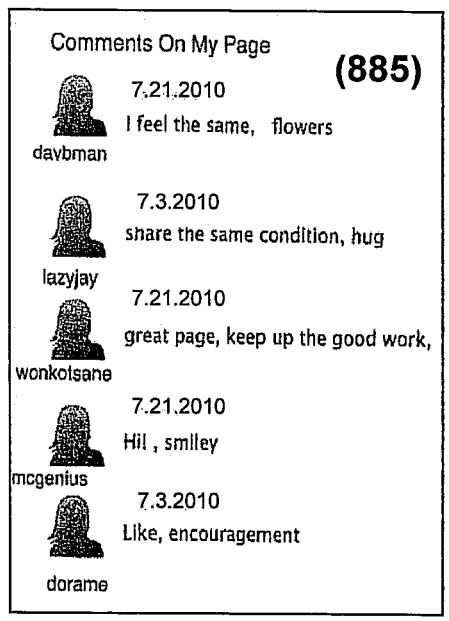
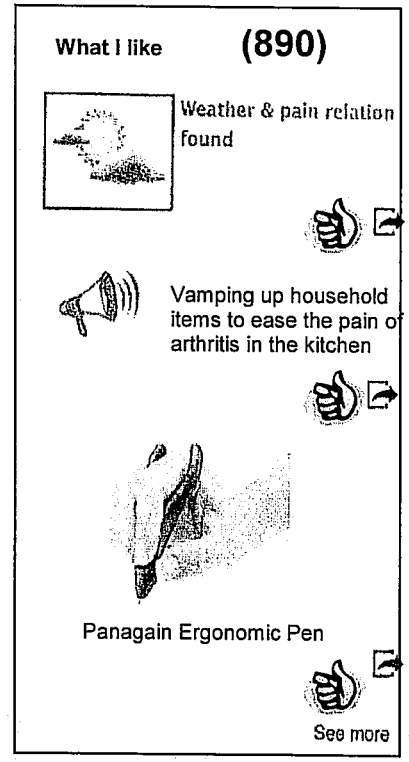
Fig. 8b

Welcome Bristoddl

COMMUNITY HOMEPAGE
Member View

Your Badges

910

My Quote for The Day
"Pain is inevitable. Suffering is optional" — 920
Browse Quotes   Let site suggest 930 — Whats new
Tip from your friends
Why it's important to know about Omega6 and Omega3

940 — Helpful answers
Uninsured? Need help paying for brand X Medicine?
Pharmaco has programs that can help. Call 1-800-11111111 or visit 950 — Your Weekly Wellness Progress Report is available
"It was a good week!
You are among the top 15% in general
Your have done 15 exercise logs this week
compared to 12 average..." Read more 960 — Tip from your friends
Vamping up household items to ease the pain of arthritis in the kitchen 970 — Help our community:
Rate the following articles, products and tips, and help others like you Universal Grip | Weather & pain relation | Tip: Walking strategies
View all

- No thanks
- I will do it later

Fig. 9a

980 {
There's a new Cooking Badge,
see how you can unlock it!
Posted 2 days ago

Choose a reply

* Choose a reply
Love it!
Thanks!

Mamilabee, thought this prod

I have shared this with others
I will check it out
Flowers
Hug

, Dr.

Send

Posted 2 days ago        Panagan Ergonomic Pen

Badge Alert

Goblin unlocked the
"All-around Wellness" badge!

Posted Tuesday Oct 19th
}

Community News

How are you doing compared to the community? You have logged 3 exercises this week. The community exercise log average is 2.5. Well done!

Read tips to help choose your best exercise and how to keep it up
Read how increasing daily activities helped another member Joshuameltz

Posted Tues Oct 19th                            } 990

Community Wisdom

Q   Answer this pain quiz and see how you are doing against
    other members and maybe you will learn a new trick or two...

Start the Quiz

Is your level of pain influenced by
weather changes?

O Yes, every time

O Sometimes

O Never happens to me     Submit

View results
} 995

Mamilabee's new quote is:

" We may run, walk, stumble, drive, or fly,
but let us never lose sight of the reason for
the journey, or miss a chance to see a rainbow on the way"

Fig. 9b

METHOD AND SYSTEM FOR AN ONLINE PATIENT COMMUNITY BASED ON "STRUCTURED DIALOG"

FIELD OF THE INVENTION

The present invention relates generally to health support services and more particularly, to a method and a system for an online health community based on "Structured Dialogs."

BACKGROUND OF THE INVENTION

Engaging consumers in sharing information from personally controlled health records (PCHR's) and patient communities for health research and patient support may promote goals of improving care and advancing public health. Understanding consumer willingness to share data is critical to advancing this model. Many entrepreneurs have originated PCHR's and patient communities for health research and patient support communities (e.g., patientslikeme.com) because of difficulties friends and/or relatives have had getting emotional and social support related to prolonged illness.

In the past there have been problems with patient community Web sites. Regulatory agencies require Adverse Event Reports whenever a patient contributes text that may be interpreted as an adverse event, and the pharmaceutical company, for example, is required to file required paperwork and conduct an investigation. MSWatch.com, a community for Multiple Sclerosis patients, was such a site. At MSWatch.com, patients could create their own multiple sclerosis treatment diary coupled with a support community of multiple sclerosis patients and experts. Despite the significant success for engaging and supporting Multiple Sclerosis patients, it appears that the host pharmaceutical company has decided to close this site due to the challenge of the mandatory monitoring of patient contributed content, although specific knowledge of the situation is not certain. Prior art FIG. 1 shows a typical Web page 100 from Web site MSWatch.com. Problematic patient input 110 is shown. Likewise, other regulatory issues like privacy and HIPAA have also hindered the use of patient communities.

Thus, such Web sites have been shut down because free discussions with patients are unworkable, and it would be advantageous to provide an improved method and system for sharing and recording patient experiences.

SUMMARY OF THE INVENTION

Accordingly, it is a principal object of the present invention to provide a patient engagement solution that adheres to strict regulatory healthcare and pharmaceutical guidelines, yet offers the full scope and strength of a patient community. Such community may also be safely coupled with a personal health management solution and personalized health content.

It is another principal object of the present invention to provide a solution with INHERENT ADHERENCE TO REGULATORY GUIDELINES using Structured Dialogs of specific choices, with no need for moderation.

1. an online health community based on Structured Dialogs that can offer pharmaceutical companies, and healthcare organizations in general, the opportunity to create online patient communities and have a dialog with their patients on their websites, without the risk of unnoticed adverse event reports by users or other privacy and regulatory issues (which is why many otherwise valuable websites had to be abandoned).
2. an interface in which users can only communicate via controlled, limited vocabulary elements such as pop-ups, drop downs, sliders, buttons, selection within fixed lists, etc. The site does not have any place to enable users to write free text and by that limits the dialogs that can be presented within the site.
3. To make the interaction more interesting and effective for patients, the community can also be coupled with a personal health and wellness management planner tool (the "Me" Layer) to enable patients to track and achieve their health activities and goals. Such a tool usually offers a personal online planner for medication, lifestyle, condition related activities and personal tasks that are usually related to the health product, drug or condition. The personal online planner would also make use of the controlled vocabulary of the Structured Dialogs to ensure the same inherent adherence to regulatory guidelines as the community. The "Me" Layer is connected via an information feed to the community enabling the patient to share personal progress updates with the community (the "We" Layer).
4. By connecting the Me and We Layers, the patients are provided with (a) a strong companion management tool for the health product or service and (b) relevant support, statistics, and information from the community.
5. The structured information within Structured Dialogs, enables further use of game dynamics, rewards, challenges, statistics (e.g., "how do I compare with the community"), etc. to support patients.
6. The We Layer and the Me Layer can also be connected to a content (e.g., health articles) selection process that based on the patient activities recorded within the "Me" Layer and the community activities within the "We" Layer offers highly personalized content selection ("Info" Layer). For example, a patient may report that he or she has started jogging via the "Me" Layer, and be provided with an article about the benefits of running for his or her condition. The "Info" Layer may be further connected to the "Me" and "We" Layers to provide personal and community references within the content (e.g., reading an article about the benefits of yoga for a condition may offer personal statistics about the patient from his or her "Me" Layer about personal yoga activities, e.g., "on average you have attended 2.5 yoga classes every week for the last 2 months" as well as community statistics, e.g., "15% of the community found yoga beneficial to reduce pain") and by thus make articles much more relevant and interesting to users.
7. Such a solution is also advantageous for mobile devices, and especially mobile touch devices, because the Structured Dialogs does not need to require typing, but just quick, limited selections, thereby enabling simplified use of such devices via touch selections.
8. The Structured Dialogs coupled with the fact that the website does not need to contain any identifying information (beyond a username and password) also protects the subscribing pharmaceutical or healthcare companies from any privacy issues and offers inherit privacy protection under regulations and guidelines such as those from HIPAA. The username can also be selected from a controlled list to fully separate the user identity from the website.

9. Beyond the marketing and support benefit to pharmaceutical and other healthcare companies, as far as establishing a community and engaging directly with patients, the website provides a source for anonymous aggregate statistics based on the Structured Dialogs from the patient community and the patient personal planner (e.g., statistics about patient acquisition, conversion, retention, adherence, health outcomes, sentiment, etc.) as well as enabling such an environment to directly recruit patients for clinical trials and other research and marketing projects via opt-in mechanisms.

A system is disclosed for an online community based on Structured Dialogs that provides a plurality of subscribing organizations the opportunity to create online communities and have a dialog with a plurality of users/patients on at least one website and/or mobile Web/app of one of said plurality of organizations, without the risk of unnoticed adverse event reports by users/patients. The system includes an interface wherein the users/patients can only communicate with Structured Dialogs elements comprising at least one of pop-ups, drop downs, buttons, sliders and other preset screen controls. The interface provides for user displays of personal health and wellness management tools. The tools include a personal component, a community component and a content component.

The personal component administers the inputs of users/patients enabling the users/patients to track and achieve their health activities and goals. The community component enables support and comparisons of the users/patients inputs with the inputs of other users/patients suffering from the same or similar infirmities and the content component can offer articles relevant to the users/patients.

The personal component may be embodied as a personal health and wellness management "Me" Layer coupled to the community. The community component is embodied as a "We" Layer displaying the output of an information feed to the "Me" Layer and the We Layer enables a user/patient to share personal experiences with the community. The content component may be embodied as an "Info" Layer providing personalized content and reference content automatically found by the system from the "Me" and "We" Layers and from internal and outside content sources. The "Info" Layer provides personalized content that may include reference information from the "Me" and the "We" Layers, e.g., and statistics that are relevant to a specific health article from the "Me" and "We" layers.

The Structured Dialogs enable use of game dynamics ("Your team lost the most amount of weight"), rewards ("You gain a badge for adherence to your medication program") and statistics based on controlled vocabulary ("How do I compare with the community") to support patients.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

For a better understanding of the invention with regard to the embodiments thereof, reference is now made to the accompanying drawings, in which like numerals designate corresponding elements or sections throughout, and in which:

FIG. 1 is a screenshot illustrating the prior art;

FIG. 5 is an article page illustrating the addition of personal and community statistics and information, constructed according to the principles of the present invention;

FIG. 6 is a schematic representation of an initial online interview of the patient in order to build a personal plan as well as a community personal page, constructed according to the principles of the present invention;

FIG. 8a is a schematic representation of a top portion of a patient's personal page, within the community constructed according to the principles of the present invention;

FIG. 8b is a schematic representation of a bottom portion of a patient's personal page, constructed according to the principles of the present invention;

FIG. 9a is a schematic representation of a top portion of a Community Homepage, Member page view, constructed according to the principles of the present invention; and FIG. 9b is a schematic representation of a bottom portion of a Community Homepage, Member page view, constructed according to the principles of the present invention.

DETAILED DESCRIPTION OF AN EXEMPLARY EMBODIMENT

The principles and operation of a method and an apparatus according to the present invention may be better understood with reference to the drawings and the accompanying description, it being understood that these drawings are given for illustrative purposes only and are not meant to be limiting.

FIG. 1 is a screenshot illustrating the prior art where consumers ask questions 100 and other consumers provide answers 110.

Figure 2:
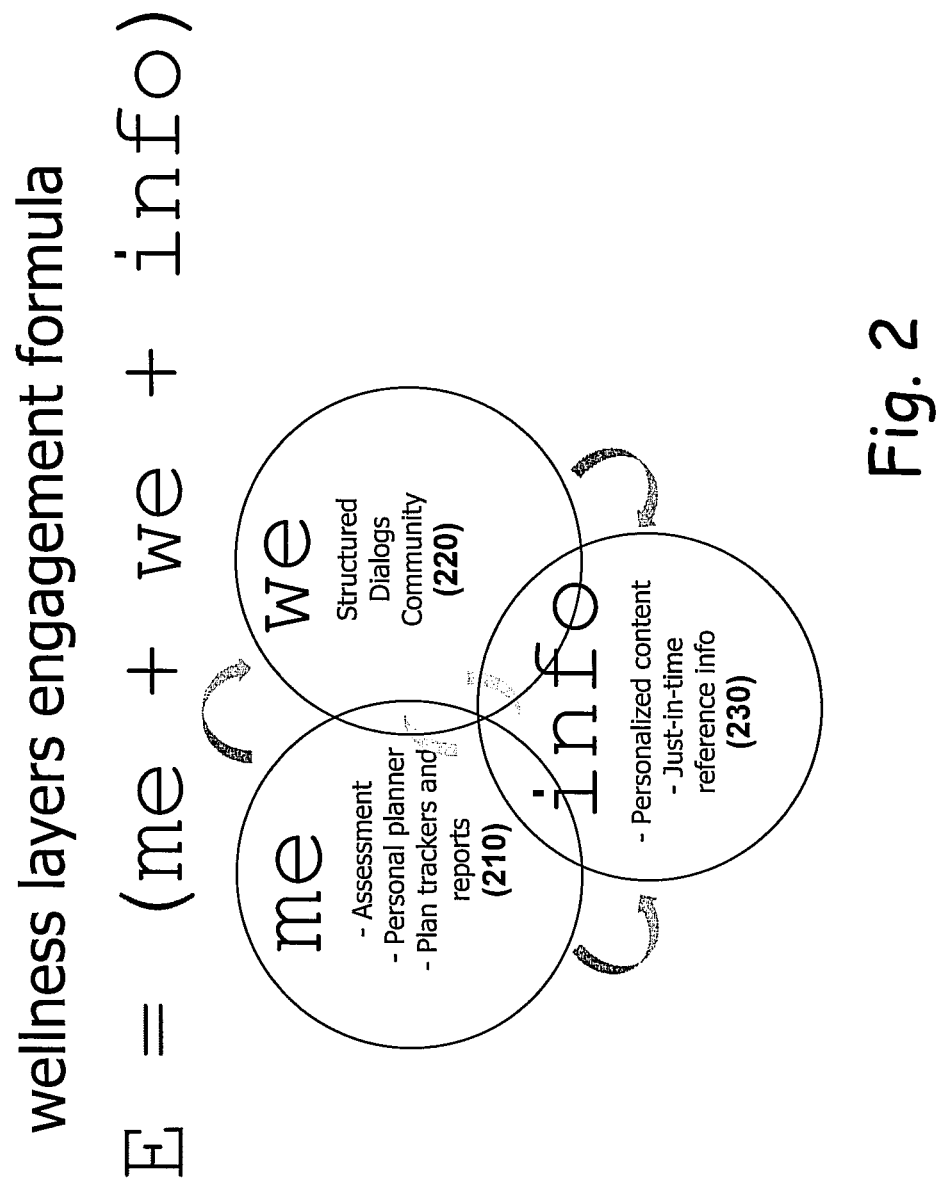
FIG. 2 is a schematic illustration of the Wellness Layers engagement formula, constructed according to the principles of the present invention.

FIG. 2 is a schematic illustration of Wellness "Layers" engagement, constructed according to the principles of the present invention. The present invention provides a patient's personal health management solution ("Me" Layer), as well as receives support from other patients via a patient community ("We" Layer) and personalized content ("Info" Layer). By connecting the Me and We Layers, the patients are provided with (a) a strong companion management tool for the health product or service and (b) relevant support, statistics, and information from the community.

The "Info" Layer may be further connected to the "Me" and "We" Layers to provide personal and community references within the content (e.g., reading an article about the benefits of yoga for a condition may offer personal statistics about the patient from his or her "Me" Layer about personal yoga activities.

The layers can be thought in the manner of physical transparency overlays, such that each contributes to an overall image when overlaid together. The "Me" Layer 210 provides assessment, a personal plan, plan trackers and reports. The "We" Layer 220 enables a controlled Structured Dialogs community for a healthcare product, for example and the "Info" Layer 230 provides personalized content with "Me" and "We" Just-In-Time reference content. "Just-In-Time" can be illustrated by an example. E.g., a patient may enter in the "Me" Layer that he or she does yoga twice a week. The system is able to automatically find and present cross-referenced relevant statistics from the We Layer, such as "Other community members who also report having Alzheimer's do yoga 1.5 times a week on average. Congratulations, you are above average in this category." The arrows provide reference to the cross feeds that occur between the Me/We/Info Layers.

Figure 3:
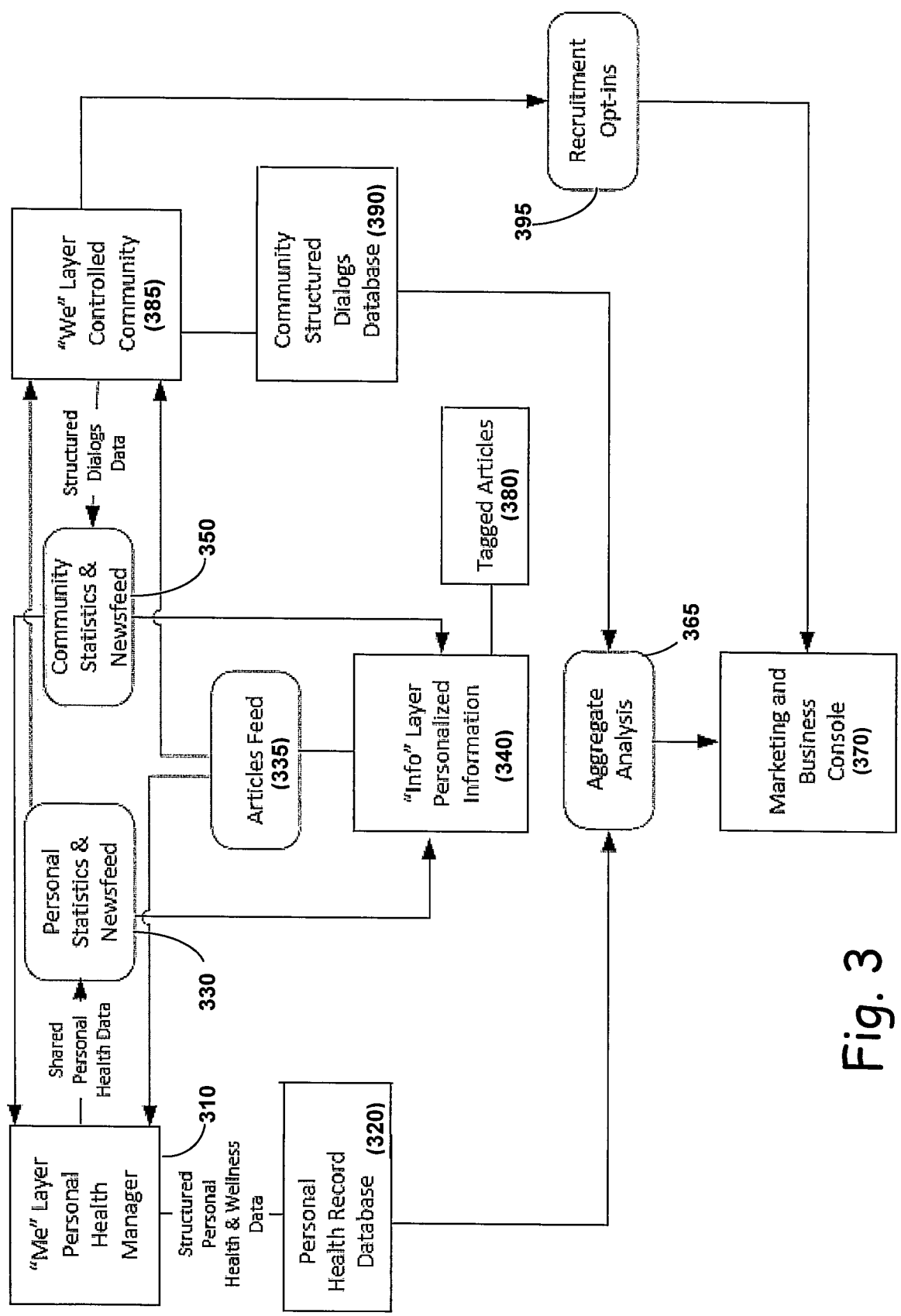
FIG. 3 is a schematic flow chart of the overall invention, constructed according to the principles of the present invention

FIG. 3 is a schematic flow chart of the overall invention, constructed according to the principles of the present invention. The "Me" Layer Personal Health Manager 310 exchanges structured data with the Personal Health Record Database 320 and is interactive with the "We" Layer Controlled Community 385, which in turn exchanges data with the Community Structured Dialogs Database 390 and is interactive with "Me" Layer 310. Both Personal Health Record Database 320 and Community Structured Dialogs Database 390 pass on data for Aggregate Analysis 365, with analyzed results passed onto the Marketing and Business console 370. "We" Layer Controlled Community 385 also provides opt-in Recruitment Options to Marketing and Business console 370. Opt-in Recruitment is basically leveraging the direct community connection to solicit volunteers for clinical trials and other patient recruitments. Such volunteers will need to opt-in and either approach the company or provide their contact information so they can be approached by the company.

"Me" Layer Personal Health Manager 310 provides Shared Personal Health Data for Personal Statistics and Newsfeed 330 to the "Info" Layer Personalized information 340. "We" Layer Controlled Community 385 provides Structured Dialogs data to the Community Statistics and Newsfeed process 350 to be shared with the "Info" Layer personalized information 340. "Info" Layer personalized information 340 receives Tagged Articles 380 and provides relevant Article Feeds 335 to both the "Me" Layer Personal Health Manager 310 and "We" Layer Controlled Community 385.

Such schematic flow shows the cross feeds between each one of the "Me", "We", and "Info" Layers as well as the aggregate statistics and recruitment option for the business console.

Figure 4:
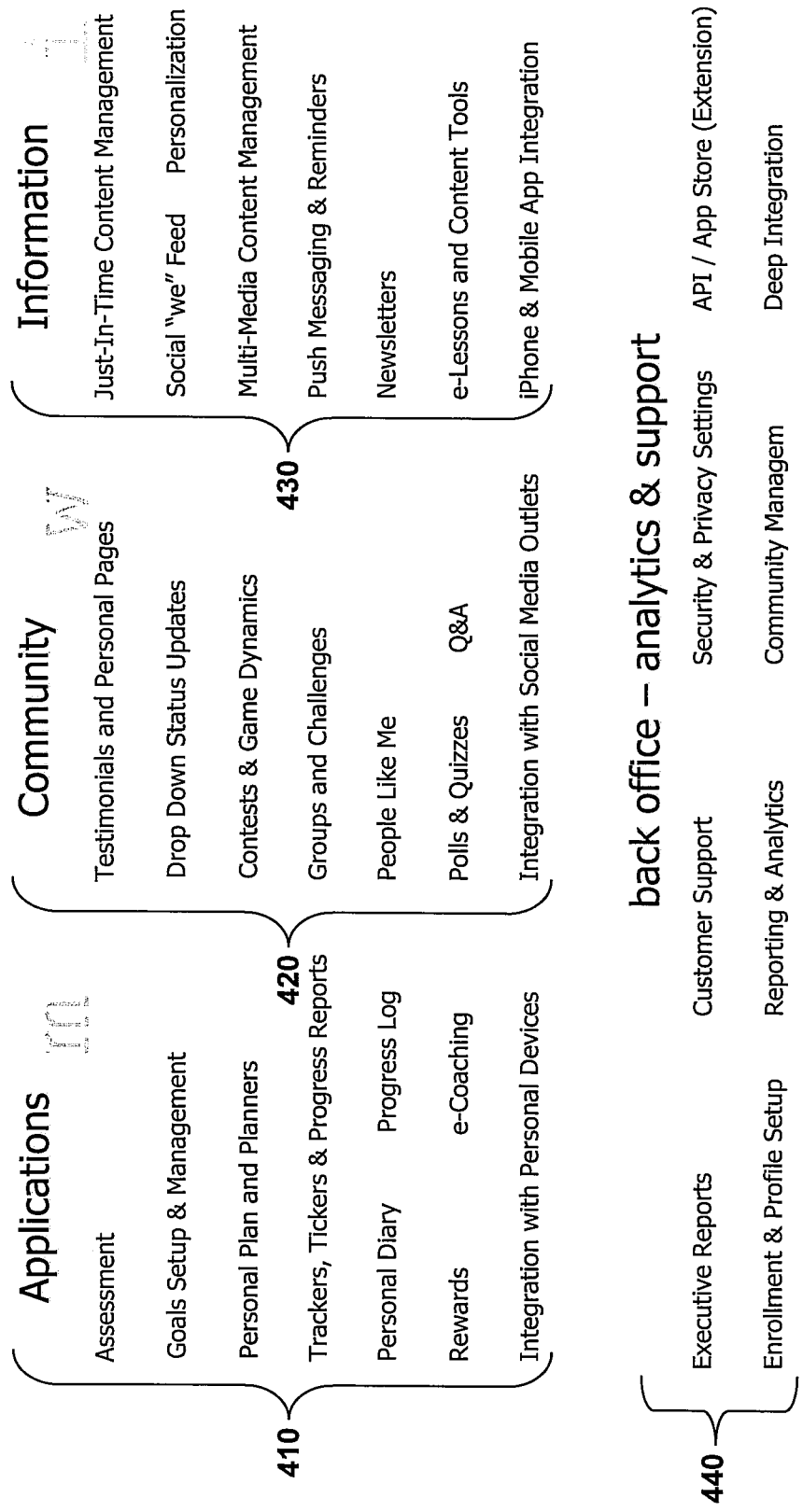
FIG. 4 is a tabular representation of application layers, community social interactions, information and back office sources of analytics and support, constructed according to the principles of the present invention.

FIG. 4 is a tabular representation of personal health management application layer ("Me layer") 410, Structured Dialogs community ("We layer") 420 and information 430 and back office sources of analytics and support 440, constructed according to the principles of the present invention. The examples in each group illustrate the content of the group.

FIG. 5 is an article page illustrating the addition of Just-In-Time reference information from the "Me" and "We" Layers into the article ("Info" Layer), constructed according to the principles of the present invention. Just-In-Time community information and a personal statistics feed 510 is presented. The entire page is a single article related to the Me and We inputs about personal and community inputs relative to therapeutic yoga practice.

FIG. 6 is a schematic representation of building a personal plan and community personal page via a personal interview, constructed according to the principles of the present invention. The structured dialog illustrates the patients inputs for the Me layer. Questions such as "Have you been diagnosed by a doctor?" 610, "How long ago were you diagnosed?" 620 and "What medications are you taking?" 630. Medication type choices are presented in an exemplary scrollable window, with a selected medication highlighted 631. Additional medications are listed 632, to be clicked, and thereby highlighted, if they are taken. The dialog asks whether the patient has made any changes to these categories to help improve your condition 633. This illustrates one example of the Structured Dialogs method for acquiring information rather than free text.

Figure 7A:
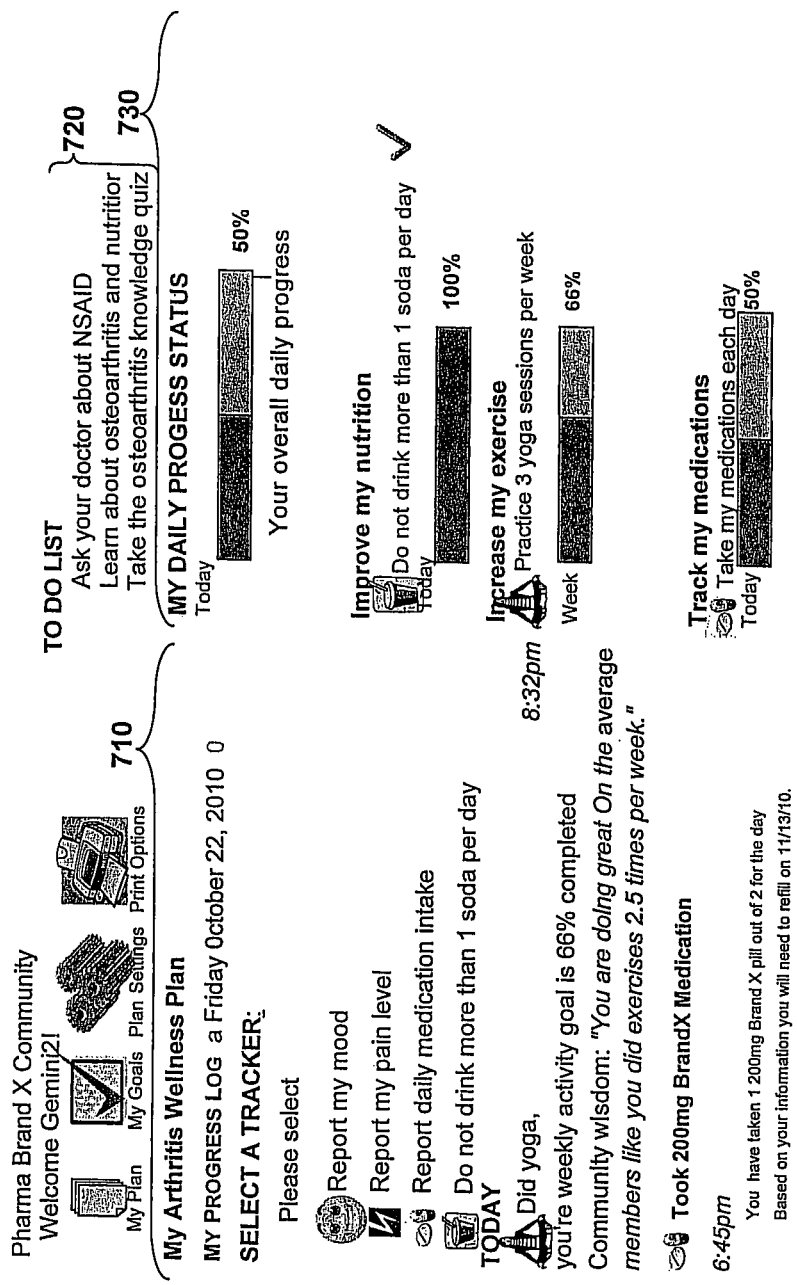
FIG. 7a is a schematic representation of logging a patient's progress within the Me Layer, constructed according to the principles of the present invention.

FIG. 7a is a schematic representation of logging an exemplary patient's progress, constructed according to the principles of the present invention. FIG. 7a shows hypothetical patient "Gemini2's" Arthritis Wellness Plan 710, including: "Progress Log", "Today's Activities" and "History". Also shown are Gemini2's "To Do List" 720 and Gemini2's "Daily Progress Status" 730. The logs and graphs of FIG. 7a are built from the Me layer input structured dialogs, such as those of FIG. 6.

Figure 7B:
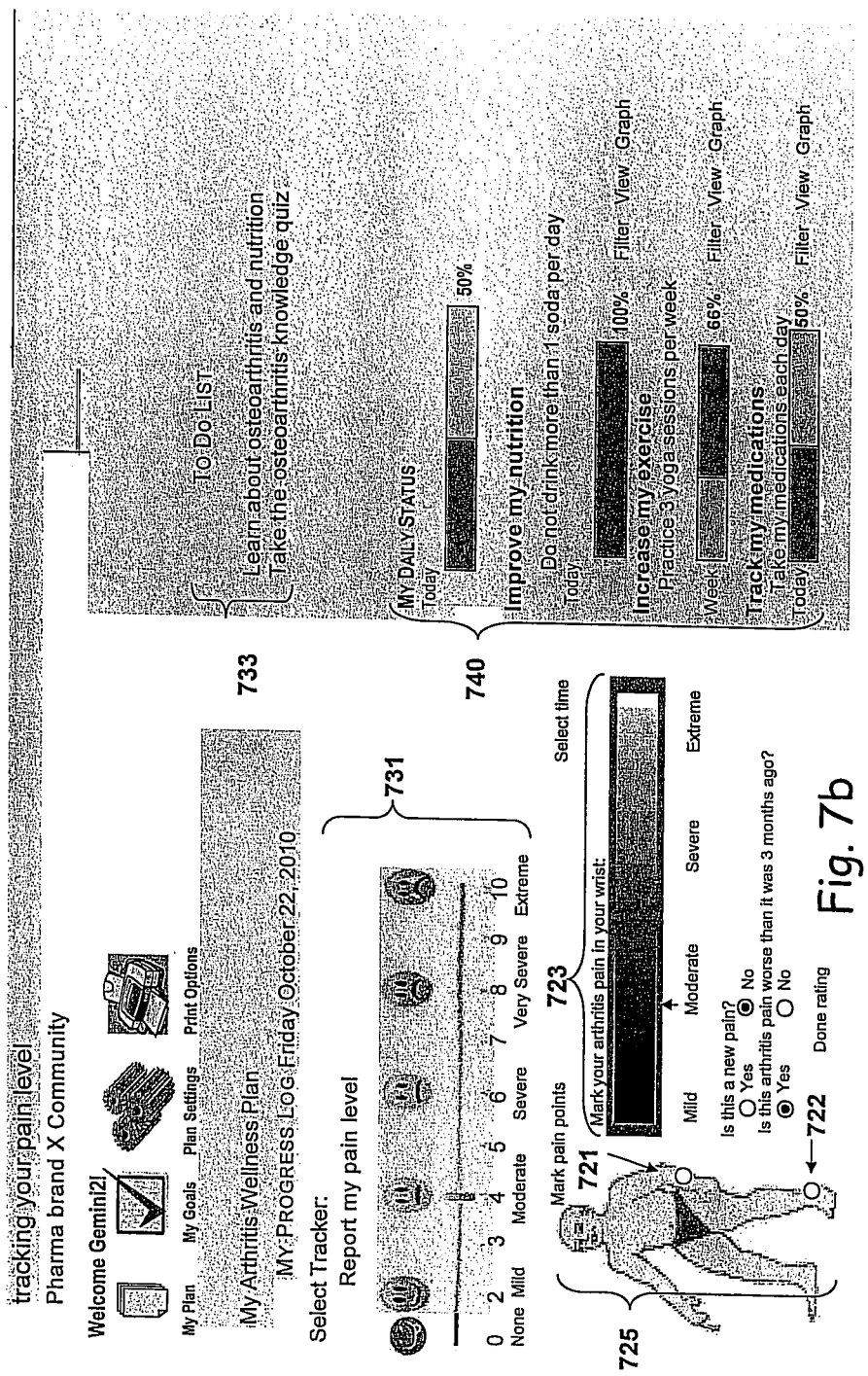
FIG. 7b is a schematic representation of examples of tracking a patient's pain level, with different controlled trackers for different conditions constructed according to the principles of the present invention.

FIG. 7b is a schematic representation of tracking a patient's pain level, constructed according to the principles of the present invention. An exemplary patient Gemini2 shows his arthritis wellness plan, where he specifically inputs his general pain level using a controlled slider 731 on a scale of 0 to 10. An example of a patient's list of tasks that need to be done 733 and periodic (e.g., daily, weekly, etc.) bar charts for "My Status" 740 are shown. The bar charts are automatically derived from the patient's inputs to the structured dialogs, as described above. Gemini2 is instructed to mark pain points 725 on the left wrist 721 and the left ankle 722, with a grayscale 723 to be marked for the wrist pain. Structured Dialogs input refers to the fact that the user can log his or her pain for that day based on controlled vocabulary and without free text. Again, the bar graphs of FIG. 7b are built from the Me layer input structured dialogs, such as those of FIG. 6.

Figure 8A:
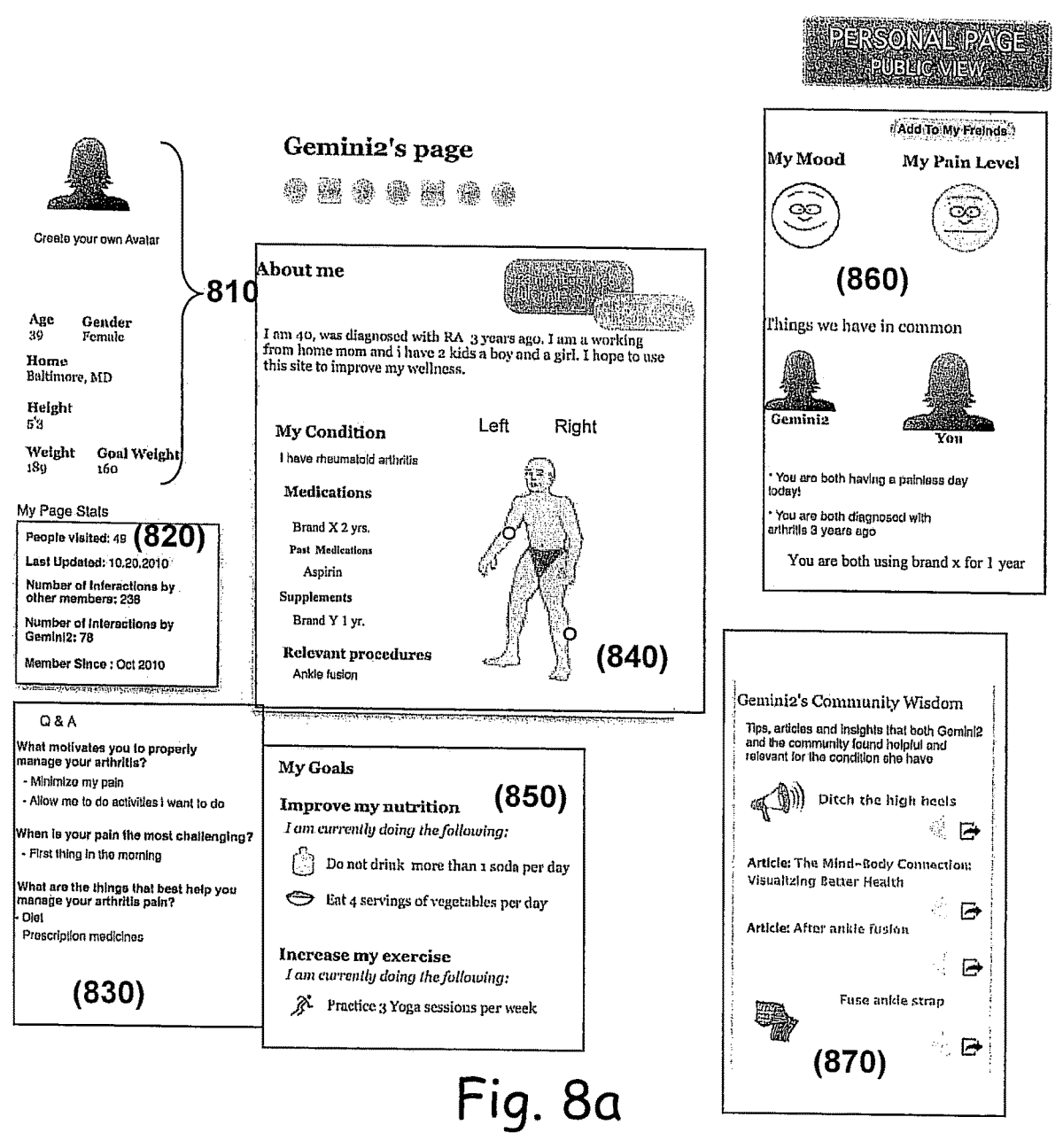

FIG. 8a is a schematic representation of a top portion of a patient's personal page as presented in the community, constructed according to the principles of the present invention. For the exemplary patient "Gemini2" a selected avatar and demographics are shown 810. Page stats 820 and typical questions and answers introducing the patient to the community 830 are provided. Information is given about "My Medical Condition" 840, summarizing the patient's personal data, medication and specific pain points. "My Medical Goals" 850 puts the patients goals for nutrition and exercise, for example, into simple sentence format. Finally, information is presented about: "Friends I have made on the website" 860, generally those with similar conditions, as well as "Community Wisdom" which provides relevant information from the community dialogs 870.

FIG. 8b is a schematic representation of a bottom portion of a patient's personal page, constructed according to the principles of the present invention. Graphical data about the patient's progress is presented 875 and a scrollable display of "My Friends" with their names/nicknames and avatars 880, combining "Me layer" inputs and pictorial representations for illustrative purposes. Using Structured Dialogs, friends can post comments 885 and various controlled items such as "I like" 890 that can be clicked for more quick exposition of thoughts, feelings, and community encouragement.

FIG. 9a is a schematic representation of a top portion of a Community Homepage, Member view page, constructed according to the principles of the present invention. The following are presented: badges the patient won 910, for example: "You gain a badge for adherence to your medication program;" an inspirational quote for the day 920, for example: "Pain is inevitable, suffering is optional;" and new relevant community information newsfeed, such as tips from friends 930 are shown. "Helpful Answers" 940, for example a helpful web site; a comparative report 950, for example comparisons to the "We layer" community; tips recommended by friends 960, for example, additional friendly advice; and a community rating facility 970, for example rating solicitations for articles, products and tips are provided.

FIG. 9b is a schematic representation of a bottom portion of a Community Homepage, Member view page, constructed according to the principles of the present invention. FIG. 9b presents more community newsfeeds: general posts and responses 980, Community News 990 and Community wisdom, which shows relevant community statistics 995.

Having described the present invention with regard to certain specific embodiments thereof, it is to be understood that the description is not meant as a limitation, since further modifications will now suggest themselves to those skilled in the art, and it is intended to cover such modifications as fall within the scope of the appended claims. The above description is an example for a specific condition, but the approach needs to change with regards to what is the "Me", "We" and "Info" for every product.

We claim:

1. A community healthcare system for sharing health information accessible via at least one website and/or mobile Web/app to improve personalized health content for user/patients of the system, the system comprising:
    an interface having
        Structured Dialogs, the Structured Dialogs comprising at least one of pop-ups, drop downs, sliders and other preset screen controls, wherein the Structured Dialogs have a controlled vocabulary without free text and wherein a plurality of users/patents using the interface are only able to communicate via the Structured Dialogs, such that the Structured Dialogs allow for the users/patients to communicate with one another,
        user displays of personal health, and
        wellness management tools, the tools comprising a personal component, a community component, and a system component,
        wherein the interface shares health information of the one or more users/patients;
    a memory comprising computer executable instructions and data;
    a processor functionally coupled to the memory and configured by the computer executable instructions, the interface executing on the processor; and
    a database that stores the health information of the users/patients,
    wherein said personal component administers the inputs of the users/patients to enable the users/patients to track and achieve their health activities and goals, said personal component embodied as a personal health and wellness management "Me" Layer coupled to said community component, wherein the inputs of the users/patients in the "Me" Layer are Structured Dialogs,
    wherein said community component compares of the users/patients inputs with the inputs of other users/patients suffering from the same or similar infirmities, said community component embodied as a "We" Layer displaying the output of an information feed to said "Me" Layer, wherein said We Layer enables a patient to share personal experiences with said community component, wherein the inputs of the "We" Layer are Structured Dialogs,
    wherein said "Me" Layer transmits an assessment, a personal plan, and/or plan trackers to the users/patients on an individualized basis,
    wherein said system component transmits articles relevant to the plurality of users/patients based upon the inputs of the users/patients, said system component is embodied as an "Info" Layer providing personalized content and reference content automatically found by the system from the "Me" and "We" Layer, to the individual users/patients,
    wherein the system adjusts personalized health content of the user/patients based on the combination of the "We", "Me" and "Info" Layers, and
wherein the "We", "Me" and "Info" Layers are application layers.

2. The system of claim 1, wherein said healthcare system is hosted by a healthcare organization.

3. The system of claim 2, wherein said healthcare organization is a pharmaceutical company.

4. The system of claim 1, wherein said at least one website does not accept free text users.

5. The system of claim 1, wherein the community component includes a personal online planner for medication, lifestyle changes, condition-related activities and personal tasks that are related to drugs or conditions.

6. The system of claim 2, wherein said Structured Dialogs enable aggregation of statistics and market analysis.

7. The system of claim 1, wherein said Structured Dialogs enable use of game dynamics, rewards and statistics based on Structured Dialogs to support users/patients.

8. The system of claim 1, wherein said system is implemented for touch screen mobile devices of said users/patients.

9. The system of claim 1, wherein the system adheres to strict regulatory healthcare and pharmaceutical guidelines.

10. The system of claim 1, wherein the system protects the plurality of users/patients from privacy issues.

11. The system of claim 1, wherein the system provides a plurality of subscribing organizations the opportunity to create online communities and have a dialog with a plurality of users/patients.

12. The system of claim 1, wherein the system operates without the risk of unnoticed adverse event reports by users/patients.

13. A computer implemented method for sharing health information to improve personalized health content for user/patients, the method executed on a processor, the method comprising:
    providing a community interface having Structured Dialogs, the Structured Dialogs comprising at least one of pop-ups, drop downs, sliders and other preset screen controls, wherein the Structured Dialogs have a controlled vocabulary without free text, wherein a plurality of users/patents using the interface are only able to communicate with one another via the Structured Dialogs, and wherein the interface shares health information of the one or more users/patients;
    providing a database that stores the health information of the users/patients;

providing a memory and a processor configured to execute the computer implemented method, the computer implemented method further comprising:

allowing said plurality of users/patients to only communicate via the Structured Dialogs on said interface;

providing user displays of personal health and wellness management tools on said interface, the tools comprising a personal component, a community component, and a system component;

administering, via said personal component, the inputs of users/patients enabling the users/patients to track and achieve their health activities and goals;

comparing, via said community component, the users/patients inputs with the inputs of other users/patients suffering from the same or similar infirmities;

providing, via said system component, articles relevant to the plurality of users/patients based upon the inputs of the users/patients, wherein said personal component embodied as a personal health and wellness management "Me" Layer coupled to said community component, wherein the inputs of the users/patients in the "Me" Layer are Structured Dialogs, said community component embodied as a "We" Layer displaying the output of an information feed to said "Me" Layer and said We Layer enabling a user/patient to share personal experiences with said community component, wherein the inputs of the "We" Layer are Structured Dialogs, said system component is embodied as an "Info" Layer providing personalized content and reference content automatically found by the system from the "Me" and "We" Layers, wherein said "Me" Layer transmits an assessment, a personal plan, and/or plan trackers to the users/patients on an individualized basis, wherein the "We", "Me" and "Info" Layers are application layers; and adjusting the personalized health content of the user/patients based on the combination of the "We", "Me" and "Info" Layers.

14. A non-transitory computer readable storage medium storing a computer program product for providing a plurality of subscribing organizations the opportunity to create online communities and have a dialog with a plurality of users/patients on at least one website and/or mobile Web/app of one of said plurality of organizations for sharing health information to improve personalized health content for user/patients, without the risk of unnoticed adverse event reports by users/patients, the non-transitory computer readable storage medium comprising:

computer executable instructions and data, the computer executable instructions able to execute a computer program able to:

provide an interface having Structured Dialogs, the Structured Dialogs comprising at least one of pop-ups, drop downs, sliders and other preset screen controls, wherein the Structured Dialogs have a controlled vocabulary without free text and wherein a plurality of users/patents using the interface are only able to communicate with one another via the Structured Dialogs, wherein the interface shares health information of the one or more users/patients;

provide a database that stores the health information of the users/patients allow said plurality of users/patients to only communicate via the Structured Dialogs on said interface;

provide user displays of personal health and wellness management tools on said interface, the tools comprising a personal component, a community component, and a system component;

administer, via said personal component, the inputs of users/patients enabling the users/patients to track and achieve their health activities and goals;

compare, via said community component, the users/patients inputs with the inputs of other users/patients suffering from the same or similar infirmities; and provide, via said system component, articles relevant to the plurality of users/patients based upon the inputs of the users/patients, wherein said personal component embodied as a personal health and wellness management "Me" Layer coupled to said community component, wherein the inputs of the users/patients in the "Me" Layer are Structured Dialogs, said community component embodied as a "We" Layer displaying the output of an information feed to said "Me" Layer and said We Layer enabling a patient to share personal experiences with said community component, wherein the inputs of the "We" Layer are Structured Dialogs, said system component is embodied as an "Info" Layer providing personalized content and reference content automatically found by the system from the "Me" and "We" Layers, wherein said "Me" Layer transmits an assessment, a personal plan, and/or plan trackers to the users/patients on an individualized basis, wherein the "We", "Me" and "Info" Layers are application layers; and adjusting the personalized health content of the user/patients based on the combination of the "We", "Me" and "Info" Layers.

* * * * *